United States Patent [19]

Schröder et al.

[11] Patent Number: 5,153,354

[45] Date of Patent: Oct. 6, 1992

[54] CYCLOHEXANE DERIVATIVES CONTAINING CARBOXYL GROUPS

[75] Inventors: Wolfgang Schröder, Dorsten; Thomas Keil, Recklinghausen, both of Fed. Rep. of Germany

[73] Assignee: Huels Aktiengesellschaft, Marl, Fed. Rep. of Germany

[21] Appl. No.: 794,045

[22] Filed: Nov. 19, 1991

[30] Foreign Application Priority Data

Jan. 18, 1991 [DE]  Fed. Rep. of Germany ....... 4101355

[51] Int. Cl.[5] ............... C07C 69/74; C07C 67/38; C08F 218/02; C08F 218/14
[52] U.S. Cl. ...................... 560/128; 560/127; 560/114; 526/330
[58] Field of Search ................. 560/128, 127

[56] References Cited

U.S. PATENT DOCUMENTS 1,703,186  2/1929  Adams ........................ 560/127
4,800,150  1/1989  Katoh .......................... 430/264

Primary Examiner—Joseph L. Schofer
Assistant Examiner—Wu C. Cheng
Attorney, Agent, or Firm—Oblon, Spivak, McClelland, Maier & Neustadt

[57] ABSTRACT

Cyclohexane derivatives containing carboxyl groups with the general structure of formula (I):

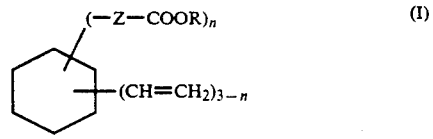

alone or in mixtures with one another, in which the substituents on the cyclohexane ring are in the 1-, 2-, and 4-positions, Z is a —$CH_2$—$CH_2$— group or a

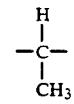

group, R is an alkyl group with 1 to 10 carbon atoms, and n is an integer of 1 to 3, are obtained by the hydrocarboxyalkylation of 1,2,4-trivinylcyclohexane and are useful as monomers for the formation of polymers.

5 Claims, No Drawings

CYCLOHEXANE DERIVATIVES CONTAINING CARBOXYL GROUPS

BACKGROUND OF THE INVENTION

1. Field of the Invention

The present invention relates to novel cyclohexane derivatives containing carboxyl groups of formula (I):

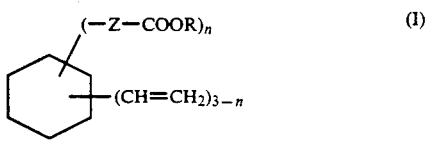

in which the substituents, $\text{-}(Z\text{-}COOR)_n$ and $\text{-}(CH=CH_2)_{3-n}$, are in the 1-, 2-, and 4-positions of the cyclohexane ring, Z is a $-CH_2-CH_2-$ group (ethylene group) or a

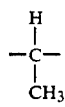

group (ethylidene group), R is an alkyl group having 1 to 10 carbon atoms, and n is an integer of 1 to 3, and mixtures thereof; a method for producing such cyclohexane derivatives; and polymers prepared from such cyclohexane derivatives.

2. Discussion of the Background

Cyclohexane derivatives containing carboxyl groups are of great interest as monomers and comonomers for the production of polymers. 1,2,4-trivinylcyclohexane, which is used as a starting material in the method according to the present invention, can be obtained, for example, according to R. Rienäcker, *Brennstoff-Chemie*, vol. 45, p. 206 (1964), by pyrolysis of 1,5,9-cylcododeca-triene.

According to DE-B 29 12 489, monoolefins with an internal carbon-carbon double bond can be hydrocarboxyalkylated in the presence of a cobalt compound as the catalyst and pyridine or a non-ortho-alkylated pyridine as the promoter, at a termperature of 165° to 195° C. and a pressure of 150,000 to 300,000 hPa (hectopascals). However, this reference provides no information concerning the behavior of dienes or polyenes under these conditions.

J. Falbe, *Synthesen mit Kohlenmonoxid*, Berlin - Heidelberg - New York, 1967, states that 1,5-cyclooctadiene is hydrocarboxyalkylated either to an unsaturated monocarboxylic acid ester or to a saturated dicarboxylic acid ester with a palladium catalyst. In the analogous hydrocarboxylation of 1,5-cyclooctadiene with a cobalt catalyst, however, only a saturated monocarboxylic acid is obtained. Therefore, of the two internal double bonds, one is hydrocarboxylated and one is hydrogenated on the cobalt catalyst.

According to U. Buller (dissertation, Technical University of Rhineland-Westphalia in Aachen, 1980), $\alpha,\omega$-dienes react with carbon monoxide and an alcohol at 130° to 140° C. to form dicarboxylic acid esters, with high selectivity.

In DE-A 38 12 184, reactive $\alpha,\omega$-dienes are hydrocarboxyalkylated on cobalt catalysts. Here, $\omega$-enecarboxylic acid esters are obtained at 100° to 200° C. and 150,000 to 350,000 hPa. Therefore, only one of the terminal position double bonds is hydrocarboxyalkylated, and one double bond is retained. However, the conversion yields of the $\alpha,\omega$-dienes are always below 50% in the examples.

Accordingly, prior to the present invention, it was not known that terminal position trienes could be hydrocarboxyalkylated. It was also unknown what products hydrocarboxyalkylation of such trienes would yield.

Thus, there remains a need for cyclohexane derivatives which contain carboxyl groups. These also remains a need for a method which produces cyclohexane derivatives which contain carboxyl groups.

SUMMARY OF THE INVENTION

Accordingly, it is one object of the present invention to provide novel cyclohexane derivatives containing carboxyl groups.

It is another object of the present invention to provide a method for preparing such cyclohexane derivatives.

It is another object of the present invention to provide polymers which are prepared from such cyclohexane derivatives.

These and other objects, which will become apparent in the course of the following detailed description, have been achieved by the inventors' discovery that 1,2,4-trivinylcyclohexane can be reacted with an alcohol having 1 to 10 carbon atoms and carbon monoxide, in the presence of a cobalt catalyst and a tertiary amine, at a temperature of 120° to 170° C., and a pressure of 150,000 to 350,000 hPa, for a time of 6 to 48 hours, to yield cyclohexane derivatives of formula (I)

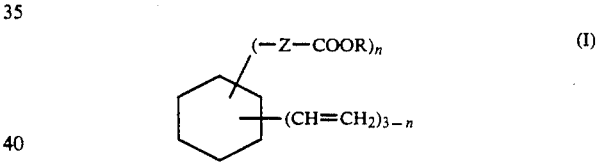

in which the substituents, $\text{-}(Z\text{-}COOR)_n$ and $\text{-}(CH=CH_2)_{3-n}$, are in the 1-, 2-, and 4-positions of the cyclohexane ring, Z is a $-CH_2-CH_2-$ group (ethylene group) or a

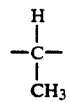

group (ethylidene group), R is an alkyl group having 1 to 10 carbon atoms, and n is an integer of 1 to 3; and that such compounds are useful as monomers for the production of polymers.

DETAILED DESCRIPTION OF THE PREFERRED EMBODIMENTS

Thus, in one embodiment, the present invention provides a method for preparing cyclohexane derivatives which contain carboxyl groups. Generally, the present method yields the present cyclohexane derivatives as a mixture. The mixture obtained by the present method generally does not contain the present compounds in approximately equal amounts. Instead, the method yields several compounds as main products, while others are formed as by-products o only in trace amounts.

The present compounds can be individually isolated from the reaction mixture, using known conventional methods, such as chromatography or fractional distillation.

However, it is to be understood that both the individual compounds and also the mixtures thereof are within the scope of the present invention.

In the hydrocarboxyalkylation, alcohols having 1 to 10 carbon atoms are suitably used. Examples include methanol, ethanol, n-propanol, isopropanol, n-butanol, isobutanol, hexanol, 2-ethylhexanol, and n-octanol. Alcohols with 1 to 4 carbon atoms are preferred, with methanol being very especially preferred. The alcohol is both a reagent and a solvent in the reaction.

Another starting material is, of course, 1,2,4-trivinylcyclohexane. Preferably, 1,2,4-trivinylcyclohexane and the alcohol are used in a molar ratio of 1:1 to 1:10, more preferably 1:2 to 1:8.

A suitable cobalt compound for the catalytic hydrocarboxyalkylation of 1,2,4-trivinylcyclohexane is hydridocobalt tetracarbonyl, $HCo(CO)_4$. However, cobalt salts, such as cobalt (II) acetate, cobalt (II) naphthenate, cobalt (II) stearate, cobalt (II) carbonate or cobalt (II) chloride, cobalt oxides or cobalt complexes, such as dicobalt octacarbonyl, can also be used.

These cobalt compounds require 0.1 to 10 mole-% hydrogen, $H_2$, based on the number of moles of carbon monoxide, in the initial phase of the hydrocarboxyalkylation. The presence of the hydrogen causes hydridocobalt tetracarbonyl to be formed under the stated reaction conditions, which is presumably the actual catalytically active compound.

A slight initial content of hydrogen is also helpful when using hydridocobalt tetracarbonyl, since hydrogen regenerates used catalyst.

It is suitable to use 0.5 to 10 mole-% of the cobalt compound, preferably 1 to 5 mole-% of the cobalt compound, based on the number of moles of 1,2,4-trivinylcyclohexane.

As the tertiary amine which acts as the promoter, pyridine and non-ortho-alkylated pyridines, such as 3- and 4-picoline, 3,4- and 3,5-lutidine, 3- and 4-ethyl pyridine or other 3- and 4-alkyl pyridines, in which alkyl can be propyl, i-propyl, butyl, i-butyl or t-butyl, can be used. Preferably, non-ortho-alkylated pyridines are used, with 4-picoline being very especially preferred.

The molar ratio of tertiary amine to cobalt compound is suitably 2:1 to 50:1.

In the hydrocarboxyalkylation, the pressure is suitably 150,000 to 350,000 hPa, preferably 200,000 to 350,000 hPa. The reaction is generally carried out in an autoclave. The pressure may be adjusted by adding or releasing CO. Thus, amount of CO present will in effect be determined by the reaction temperature and pressure selected.

In a first preferred embodiment, the present invention relates to compounds with the general structure of formula (II):

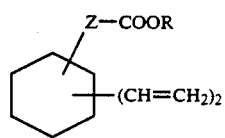
(II)

alone or in mixtures with one another, their production, and polymers prepared from such compounds.

For the production of the compounds of formula (II), 1,2,4-trivinylcyclohexane is reacted with an alcohol having 1 to 10 carbon atoms and carbon monoxide, in the presence of a cobalt catalyst and a tertiary amine, at a temperature of 120° to 140° C., and a pressure of 150,000 to 350,000 hPa, for a time of 6 to 18 hours.

In this embodiment, a product mixture is obtained which generally contains compounds having the structures of formulae (V)–(X):

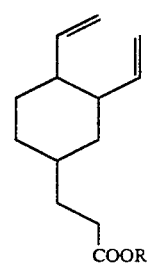
(V)

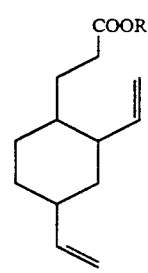
(VI)

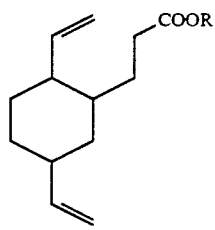
(VII)

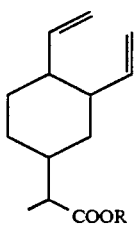
(VIII)

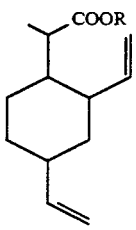
(IX)

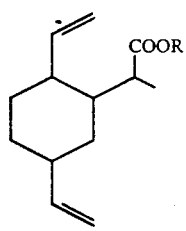  (X)

In another preferred embodiment, the present invention relates to compounds with the general structure of formula (III):

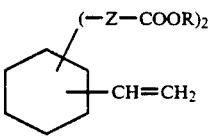  (III)

alone or in mixtures with one another, their production, and polymers prepared from such compounds.

For the production of the compounds of formula (III), 1,2,4-trivinylcyclohexane is reacted with an alcohol having 1 to 10 carbon atoms and carbon monoxide, in the presence of a cobalt catalyst and a tertiary amine, at a temperature of 130° to 160° C., and a pressure of 150,000 to 350,000 hPa, for a time of 12 to 24 hours.

In this embodiment, a product mixture is obtained which generally contains compounds having the structures of formulae (XI)–(XXII):

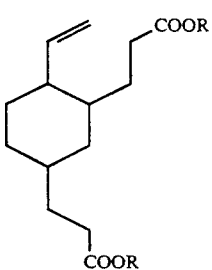  (XI)

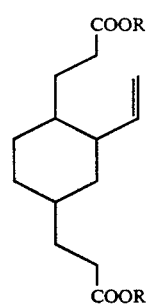  (XII)

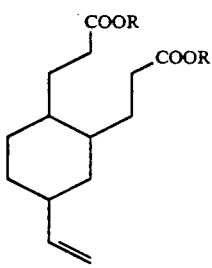  (XIII)

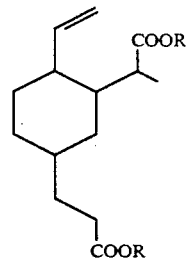  (XIV)

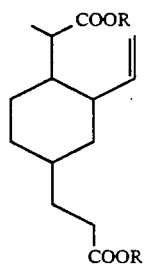  (XV)

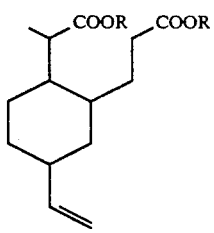  (XVI)

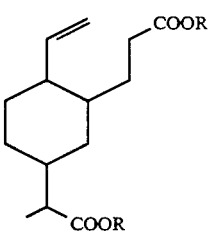  (XVII)

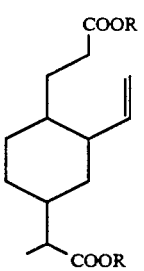  (XVIII)

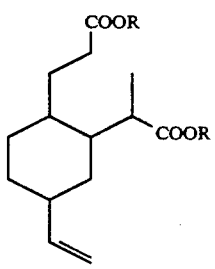  (XIX)

(XX) 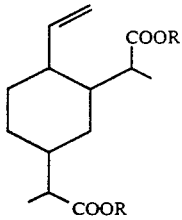

(XXIV) 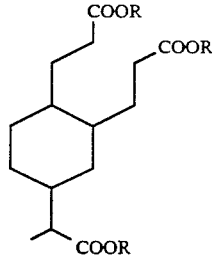

(XXI) 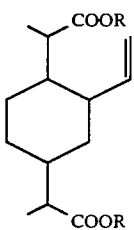

(XXV) 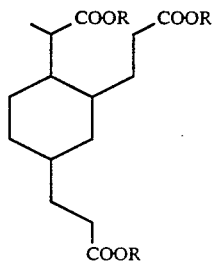

(XXII) 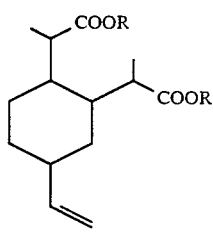

(XXVI) 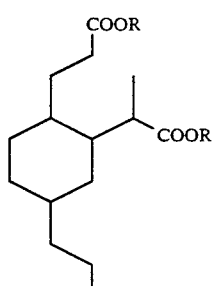

In a third preferred embodiment, the invention relates to compounds with the general structure of formula (IV)

(IV) 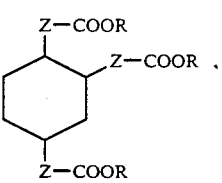

alone or in mixtures with one another, their production and polymers prepared from such compounds.

For the production of the compounds of formula (IV), 1,2,4-trivinylcyclohexane is reacted with an alcohol having 1 to 10 carbon atoms and carbon monoxide, in the presence of a cobalt catalyst and a tertiary amine, at a temperature of 130° to 170° C., and a pressure of 150,000 to 350,000 hPa, for a time of 36 to 48 hours.

In this embodiment, a product mixture is obtained which generally contains compounds having the structures of formulae (XXIII)-(XXX):

(XXIII) 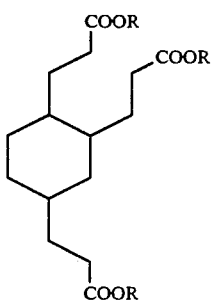

(XXVII) 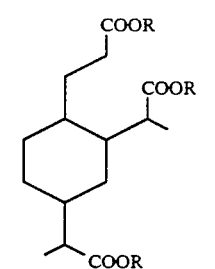

(XXVIII)

(XXIX) 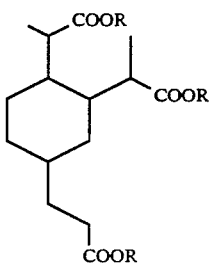

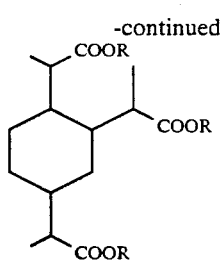

(XXX)

The method according to the present invention generally yields the present cyclohexane derivatives containing carboxyl groups in high yields, with great selectivity.

The compounds of formula (II) are obtained with a selectivity of more than 75%. The compounds of formula (III) are obtained with a selectivity of more than 55%, at a yield of more than 90%. The production method according to the present invention also yields the compounds of formula (IV) in a yield of more than 95%, with a selectivity of more than 75%.

In another embodiment, the present invention relates to polymers prepared from the present cyclohexane derivatives and a method for preparing such polymers. The present cyclohexane derivatives containing carboxyl groups can be used alone or in mixtures with one another, as monomers or comonomers, in any conventional polymerization or polycondensation process.

In the polymerization of the present cyclohexane derivatives, comonomers such as ethylene, propene, isobutene, 1-butene, 1-pentene, isoprene or butadiene, are preferably also used.

Other suitable comonomers are, for example, acrylic acid, $C_{1-4}$-alkyl acrylic acid esters, acrylic acid nitrile, acrylamide, N-$C_{1-4}$-alkyl acrylic acid amides, methacrylic acid, $C_{1-4}$-alkyl methacrylic acid esters, methacrylamide, N-$C_{1-4}$-alkyl methacrylic acid amides, maleic acid anhydride, $C_{1-4}$-alkyl maleic acid half esters or whole esters, maleic acid amide, N-$C_{1-4}$-alkyl maleic acid amides, maleimide, N-$C_{1-4}$-alkyl maleic acid imides, vinyl acetate, acrylonitrile, methacrylonitrile, styrene, α-methylstyrene, vinyl chloride, vinyl fluoride or vinylidene fluoride.

The present cyclohexane derivatives containing carboxyl groups can also be used alone or in mixtures with one another, as monomers, in polycondensation processes. Thus, they can be used for the production of alkyd resins, polyesters (with, e.g., $C_{1-8}$-alkylene diols, such as ethylene glycol, propylene glycol, butylene glycol, and 1,6-hexanediol), or polyamides (with, e.g., $C_{1-8}$-alkylene diamines, such as 1,6-hexanediamine). They can also be components of epoxy resins or improve lubricants containing ester groups.

The products according to the present invention can also be used for the synthesis of pharmaceutical products, cosmetics, aroma substances and plant protectants.

The polymers and polycondensates prepared from the present cyclohexane derivatives are useful for the production of molded articles. Such molded articles may be produced by any of the conventional techniques for preparing molded articles.

Having generally described this invention, a further understanding can be obtained by reference to certain specific examples which are provided herein for purposes of illustration only and are not intended to be limiting unless otherwise specified.

EXAMPLES

In the examples, a 5 liter VA steel autoclave is used. The reaction components 1,2,4-trivinylcyclohexane, alcohol, cobalt (II) salt and 4-picoline are added in and brought to the reaction temperature. Then hydrogen pressure is applied, with the overall pressure being built up by the application of carbon monoxide pressure. The pressure drop during the reaction is equalized by constant addition of carbon monoxide.

After the reaction is complete, the mixture is cooled to room temperature and brought to atmospheric pressure. The yields determined by gas chromatography are indicated in mole-%, based on the amount of 1,2,4-trivinylcyclohexane used.

EXAMPLE 1

Amount weighed in 908.9 g (5.6 mole) of 1,2,4-trivinylcyclohexane
717.7 g (22.4 mole) of methanol
62.6 g (0.672 mole) of 4-picoline
99.0 g (0.168 mole) of Co (II) naphthenate (10% Co)

Reaction conditions $p_{H2}$ = 10,000 hPa (initially); $p_{tot}$ = 280,000 hPa
Reaction temperature: 130° C.; reaction time: 12 h Compounds having the structure of formula (II) are obtained with 77.0% selectivity. The remainder contains isomerized initial product and compounds with the structure of formula (III).

The mixture was purified by fractional distillation and collection of the fraction distilling at 62° to 70° C. and 0.03 hPa.

EXAMPLE 2

Amount weighed in 762.8 g of 1,2,4-trivinylcyclohexane
903.5 g of methanol
52.5 g of 4-picoline
83.1 g of Co (II) naphthenate (10% Co)

Reaction conditions $p_{H2}$ = 10,000 hPa (initially); $p_{tot}$ = 280,000 hPa
Reaction temperature: 130° C.; reaction time: 12 h Compounds having the structure of formula (II) are obtained with 81.1% selectivity.

EXAMPLE 3

Amount weighed in 762.8 g of 1,2,4-trivinylcyclohexane
903.5 g of methanol
52.5 g of 4-picoline
83.1 g of Co (II) naphthenate (10% Co)

Reaction conditions $p_{H2}$ = 5,000 hPa (initially); $p_{tot}$ = 280,000 hPa
Reaction temperature: 130° C.; reaction time: 12 h Compounds having the structure of formula (II) are obtained with 78.0% selectivity.

EXAMPLE 4

Amount weighed in 990.0 g ( 6.1 mole) of 1,2,4-trivinylcyclohexane 625.4 g (19.5 mole) of methanol
68.2 g (0.73 mole) of 4-picoline
107.8 g (0.183 mole) of Co (II) naphthenate (10% Co)

Reaction conditions $p_{H2}$=5,000 hPa (initially); $p_{tot}$=280,000 hPa
Reaction temperature: 130° C.; reaction time: 24 h Compounds having the structure of formula (III) are obtained at a yield of 90.6% with 59.3% selectivity. The remainder contains isomerized initial product, monohydrocarboxymethylation product and trihydrocarboxymethylation product.

The mixture was purified by fractional distillation and collection of the fraction distilling at 103° to 118° C. and 0.03 hPa.

EXAMPLE 5

Amount weighed in 990.0 g of 1,2,4-trivinylcyclohexane
625.4 g of methanol
68.2 g of 4-picoline
107.8 g of Co (II) naphthenate (10% Co)

Reaction conditions $p_{H2}$=5,000 hPa (initially); $p_{tot}$=280,000 hPa
1st stage 130° C./12 h
2nd stage 140° C./12 h Compounds having the structure of formula (III) are obtained at a yield of more than 98%, with 67.1% selectivity.

EXAMPLE 6

Amount weighed in 990.0 g of 1,2,4-trivinylcyclohexane
625.4 g of methanol
68.2 g of 4-picoline
107.8 g of Co (II) naphthenate (10% Co)

Reaction conditions $p_{H2}$=10,000 hPa (initially); $p_{tot}$=280,000 hPa
Reaction temperature: 150° C.; reaction time: 12 h Compounds having the structure of formula (III) are obtained at a yield of more than 99%, with 62.0% selectivity.

EXAMPLE 7

Amount weighed in 990.0 g of 1,2,4-trivinylcyclohexane
625.4 g of methanol
68.2 g of 4-picoline
107.8 g of Co (II) naphthenate (10% Co)

Reaction conditions $p_{H2}$=10,000 hPa (initially); $p_{tot}$=280,000 hPa
Reaction temperature: 160° C.; reaction time: 12 h Compounds having the structure of formula (III) are obtained at a yield of more than 99%, with 59.0% selectivity.

EXAMPLE 8

Amount weighed in 1,136.1 g of 1,2,4-trivinylcyclohexane
471.0 g of methanol
78.2 g of 4-picoline
123.8 g of Co (II) naphthenate (10% Co)

Reaction conditions $p_{H2}$=10,000 hPa (initially); $p_{tot}$=280,000 hPa
Reaction temperature: 140° C.; reaction time: 12 h Compounds having the structure of formula (III) are obtained at a yield of more than 96%, with 57.0% selectivity.

EXAMPLE 9

Amount weighed in 990.0 g (6.1 mole) of 1,2,4-trivinylcyclohexane
625.4 g (19.5 mole) of methanol
68.2 g (0.73 mole) of 4-picoline
107.8 g (0.183 mole) of Co (II) naphthenate (10% Co)

Reaction conditions $p_{H2}$=10,000 hPa (initially); $p_{tot}$=280,000 hPa
1st stage 130° C./24 h
2nd stage 160° C./24 h Compounds having the structure of formula (IV) are obtained at a yield of more than 99%, with 78.4% selectivity. The remainder contains di-hydrocarboxymethylation product and products with a high boiling point.

The mixture was purified by fractional distillation and collection of the fraction distilling at 145° to 158° C. and 0.04 hPa.

EXAMPLE 10

Amount weighed in 990.0 g of 1,2,4-trivinylcyclohexane
625.4 g of methanol
68.2 g of 4-picoline
107.8 g of Co (II) naphthenate (10% Co)

Reaction conditions $p_{H2}$=10,000 hPa (initially); $p_{tot}$=280,000 hPa
1st stage 130° C./24 h
2nd stage 170° C./24 h Compounds having the structure of formula (IV) are obtained at a yield of more than 99%, with 80.0% selectivity.

EXAMPLE 11

Amount weighed in 973.8 g of 1,2,4-trivinylcyclohexane
595.9 g of methanol
89.4 g of 4-picoline
141.8 g of Co (II) naphthenate (10% Co)

Reaction conditions $p_{H2}$=10,000 hPa (initially); $p_{tot}$=280,000 hPa
1st stage 130° C./24 h
2nd stage 170° C./24 h Compounds having the structure of formula (IV) are obtained at a yield of more than 99%, with 81.8% selectivity.

EXAMPLE 12

Amount weighed in 1,006.3 g of 1,2,4-trivinylcyclohexane
615.8 g of methanol
69.3 g of 4-picoline
109.6 g of Co (II) naphthenate (10% Co)

Reaction conditions $p_{H2}$ = 10,000 hPa (initially); $p_{tot}$ = 280,000 hPa
1st stage 140° C./24 h
2nd stage 170° C./24 h Compounds having the structure of formula (IV) are obtained at a yield of more than 99%, with 77.0% selectivity.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A compound having formula (I):

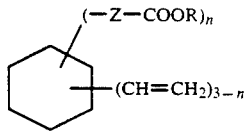

wherein substituents $-(Z-COOR)_n$ and $-(CH=CH_2)_{3-n}$ on the cyclohexane ring are in the 1-, 2-, and 4-positions, Z is a —CH$_2$CH$_2$— group or a

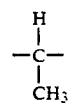

group, R is an alkyl group having 1 to 10 carbon atoms, and n is an integer of 1 to 3; and mixtures thereof.

2. A compound of claim 1, having formula (II):

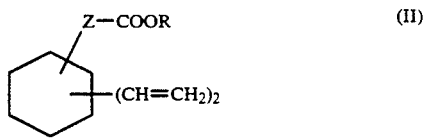

and mixtures thereof.

3. The compound of claim 1, having formula (III)

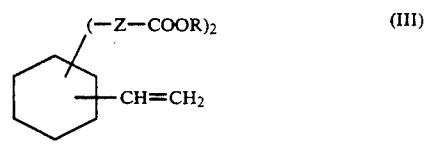

and mixtures thereof.

4. The compound of claim 1, having formula (IV):

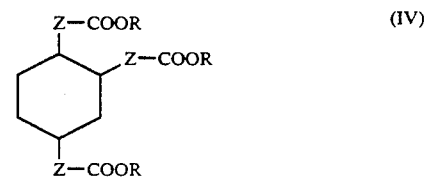

and mixtures thereof.

5. The compound of claim 1, wherein R is a methyl group.

* * * * *